United States Patent [19]

Dawson et al.

[11] Patent Number: 5,266,594
[45] Date of Patent: Nov. 30, 1993

[54] INHIBITORS OF NITRIC OXIDE SYNTHASE AND USE THEREOF TO PREVENT GLUTAMATE NEUROTOXICITY

[76] Inventors: Valina L. Dawson; Ted M. Dawson, both of 13 Campton Ct., Baltimore, Md. 21236; Edythe D. London, 41 Jones Falls Ter., Baltimore, Md. 21209; David S. Bredt, 15 Andrews Pl., Baltimore, Md. 21201; Solomon H. Snyder, 3801 Canterbury Rd., Apt. 1001, Baltimore, Md. 21218

[21] Appl. No.: 881,900

[22] Filed: May 12, 1992

[51] Int. Cl.$^5$ .............................................. A61K 31/20
[52] U.S. Cl. ..................................................... 514/560
[58] Field of Search ........................................ 514/560

[56] References Cited

PUBLICATIONS

Albin et al., 1990, "Abnormalities of striatal projection neurons and N-methyl-D-aspartate receptors in presymptomatic Huntington's disease," *N. Engl. J. Med.*, 322:1293-1298.
Beal et al., 1991, "Chronic quinolinic acid lesions in rats closely mimic Huntington's disease," *J. Neuroscience,* 11:1649-1659.
Beal et al., 1989, "Quinolinic acid striatal lesions in primates as a model of Huntington's disease," *Ann. Neurol.*, 26:137.
Choi, 1990, "Methods for antagonizing glutamate neurotoxicity," *Cerebrovasc. Brain Metab. Rev.*, 2:105-147.
Choi, 1988, "Glutamate neurotoxicity and diseases of the nervous system," *Neuron*, 1:623-634.
Coyle and Schwarcz, 1976, "Lesions of striatal neurons with kainic acid provides a model for Huntington's chorea," *Nature*, 263:244-246.
Greenamyre et al., 1985, "Alterations in L-glutamate binding in Alzheimer's and Huntington's disease," *Science, 227:1496-1499.*
Gardiner et al., 1990, "Regional and cardiac haemodynamic effects of $N^G$-nitro-L-arginine methyl ester in conscious, Long Evans rats," *Br. J. Pharmacol.*, 101(3):625-631.
McGeer and McGeer, 1976, "Alterations in L-glutamate binding in Alzheimer's and Huntington's disease," *Science*, 227:1496-1499.
Plaitakis and Yahr, 1982, "Abnormal glutamate metabolism in an adult-onset degenerative neurological disorder," *Science*, 216:193-196. References Implicating Glutamate Neurotoxicity in Neurodegenerative Disease.
Plaitakis et al., 1988, "The neuroexcitotoxic amino acids glutamate and aspartate are altered in the spinal cord and brain in amyotrophic lateral sclerosis," *Ann. Neurol.*, 24:445-449.
Rothstein et al., 1990, "Abnormal excitatory amino acid metabolism in amyotrophic lateral sclerosis," *Ann. Neurol.*, 28:18-25.
Schwarcz et al., 1983, "Quinolinic acid: an endogenous metabolite that produces axon-sparing lesions in rat brain," *Science*, 219:316-318.
Young, 1988, "NMDA receptors losses in putamen from patients with Huntington's disease," *Science*, 241:981-983.
Dawson et al., *Proc. Natl. Acad. Sci. USA, 1991, 88:6368-6371.*
Dawson et al., *J. Neuroscience,* in press, 1993.
Nowicki et al., *Eur. J. Pharmac.*, 1991, 204:339-340.
Trifiletti, *Eur. J. Pharmac.* 1992, 218:197-198.
Chem. Abst. 114-59571n (1991).
Useful Information On Alzheimer's Disease, U.S. Dept. HHS (1990).

*Primary Examiner*—S. J. Friedman
*Attorney, Agent, or Firm*—Banner, Birch, McKie and Beckett

[57] ABSTRACT

Inhibitors of nitric acid synthase can be used to prevent neurotoxicity mediated through glutamate receptors. Nitric oxide synthase inhibitors can be used therapeutically in the treatment of vascular stroke and neurodegenerative disorders such as Alzheimer's disease and Huntington's disease.

18 Claims, 6 Drawing Sheets

INHIBITORS OF NITRIC OXIDE SYNTHASE AND USE THEREOF TO PREVENT GLUTAMATE NEUROTOXICITY

This invention was made with government support. The government retains certain rights in this invention.

FIELD OF THE INVENTION

The invention relates to the use of inhibitors of nitric oxide synthase to prevent glutamate neurotoxicity.

BACKGROUND OF THE INVENTION

Nitric Oxide (NO) was originally identified in vascular endothelial cells (Palmer et al. (1987) Nature 327: 524–526 and Palmer et al. (1988) Nature 333: 664–666) and has been identified as being identical to endothelium-derived relaxing factor (Moncada et al. (1989) Biochem. Pharmacol. 38: 1709–1715; Furchgott (1990) Acta Physiol. Scand. 139: 257–270 and Ignarro (1990) Annu. Rev. Pharmacol. Toxicol. 30: 535–560). Besides endothelial cells, NO formation has been demonstrated in macrophages (Hibbs et al. (1987) Science 235: 473–476 and Marletta et al. (1988) Biochemistry 27: 8706–8711), neutrophils (McCall et al. (1989) Biochem. J. 262: 293–297; Salvemini et al. (1989) Proc. Natl. Acad. Sci. USA 86: 6328–6332 and Wright et al. (1989) Biochem. Biophys. Res. Commun. 160: 813–819), some tumor cells (Amber et al. (1988) J. Leuk. Biol. 44: 58–65), adrenal glands (Palacios et al. (1989) Biochem. Biophys. Res. Commun. 165: 802–809), Kupffer cells (Billiar et al. (1989) J. Exp. Med. 169: 1467–1472) and in brain tissue (Garthwaite et al. (1988) Nature 336: 385–388; Knowles et al. (1989) Proc. Natl. Acad. Sci. USA 86: 5159–5162 and Bredt and Snyder (1989) Proc. Natl. Acad. Sci. USA 86: 9030–9033).

Endothelium derived NO relaxes the smooth muscles of blood vessels (Palmer et al. (1987) Nature 327: 524–526 and Ignarro et al. (1987) Proc. Natl. Acad. Sci. USA 84: 9265–9269) and inhibits platelet adhesion (Radomski et al. (1987) Biochem. Biophys. Res. Commun. 148: 1482–1489). NO production by cocultures of Kupffer cells and hepatocytes mediates inhibition of hepatocyte protein synthesis (Billiar et al. (1989) J. Exp. Med. 169: 1467–1472). NO is responsible for mediating the cytotoxic effects of macrophages and neutrophils (Hibbs et al. (1987) J. Immunol. 138: 550–556). NO has also been shown to be a major neuronal messenger in the brain (Bredt and Snyder (1989) Proc. Natl. Acad. Sci USA 86: 9030–9033). The meditation of functions of tissues as diverse as the brain, endothelium and blood cells indicates a wide-spread role for NO as a messenger molecule.

NO is formed by nitric oxide synthetase (NOS) from L-arginine with stoichiometric formation of L-citrulline. Studies have shown that a guanidino nitrogen of L-arginine is used to form NO (Iyengar et al. (1987) Proc. Natl. Acad. Sci USA 84: 6369–6373; Palmer et al. (1988) Nature 333: 664–666 and Marletta et al. (1988) Biochemistry 27: 8706–8711).

The formation of NO appears to involve the same or a similar enzyme in brain and endothelial cells but a different enzyme in macrophages. The brain-endothelium enzyme has been found to require calcium and calmodulin for activity (Bredt and Snyder (1990) Proc. Natl. Acad. Sci. USA 87: 682–685). The macrophage enzyme does not require calcium-calmodulin but does require tetrahydrobiopterin for activity (Tayeh and Marletta (1989) J. Biol. Chem. 264: 19654–19658; Soo Kwon et al. (1989) J. Biol. Chem. 264: 20496–20501).

The brain (i.e., calmodulin-dependent) NOS enzyme (EC 1.14.23.-) has been purified to homogeneity from rat brain, revealing a 150,000 kD protein (Bredt and Snyder (1990) Proc. Natl. Acad. Sci. USA 87: 682–685). The purification and molecular cloning of calmodulin-dependent NOS, as well as the preparation of antibodies immunoreactive with calmodulin-dependent NOS, is described in U.S. application Ser. No. 642,002, the disclosure of which is hereby incorporated by reference.

In addition to the differences between NOS activities in brain and endothelial cells as compared to macrophages, the regulation of NOS expression appears to differ as well. The synthesis of NO does not occur in macrophages unless they have been exposed to endotoxin (e.g., bacterial lipopolysaccharide) or cytokine (e.g., interferon-$\gamma$, -$\beta$ or -$\alpha$, tissue necrosis factor-$\alpha$ or -$\beta$). However, in the brain and vascular endothelium, NOS is present without exposure to inducing agents (Knowles et al. (1990) Biochem. J. 270: 833–836). The arginine derivative L-N$^\omega$-nitroarginine (NO$_2$Arg) has been described as being a competitive inhibitor of NOS (Moore (1990) Br. J. Pharmacol. 99: 408–412).

NO has been demonstrated to mediate neuronal relaxation of intestines (Bult et al. (1990) Nature 345: 346–347; Gillespie et al. (1989) Br. J. Pharmacol. 98: 1080–1082 and Ramagopal and Leighton (1989) Eur. J. Pharmacol. 174: 297–299) and to mediate stimulation by glutamate of cGMP formation (Bredt and Snyder (1989) Proc. Natl. Acad. Sci. USA 86: 9030–9033). Glutamate, the major excitatory neurotransmitter in the brain, acts through several receptor subtypes, some of which stimulate the formation of cGMP (Ferrendelli et al. (1974) J. Neurochem. 22: 535–540). Glutamate, acting at N-methyl-D-aspartate (NMDA) subtype of receptors, is responsible for neurotoxic damage in vascular strokes. Selective antagonists of NMDA glutamate receptors prevent neuronal cell death in animal models of hypoxic-ischemic brain injury (Choi (1990) J. Neurosci. 10: 2493–2501). Glutamate neurotoxicity has also been implicated in neurodegenerative disorders such as Alzheimer and Huntington diseases (Choi (1990) J. Neurosci. 10: 2493–2501 and Meldrum and Garthwaite (1990) Trends in Pharmacol. Sci. 11: 379–387).

An effective method of preventing, treating or ameliorating diseases caused by glutamate neurotoxicity is needed in the art.

SUMMARY OF THE INVENTION

It is an object of the invention is to provide a method of treating diseases caused by glutamate neurotoxicity.

It is another object of the invention to provide a method of preventing or treating vascular stroke.

Another object of the invention is to provide a method of treating a neurodegenerative disease, such as Huntington's disease, Alzheimer's disease and Parkinson's disease.

These and other objects of the invention are provided by one or more of the embodiments described below.

In one embodiment of the invention, a method of preventing or treating diseases caused by glutamate neurotoxicity is provided, which method comprises administering to a mammal in need thereof a therapeutically effective amount of an NOS inhibitor.

In another embodiment of the invention, a method of preventing or treating vascular stroke in a mammal, in particular a human patient, is provided, which comprises administering a therapeutically effective amount of an NOS inhibitor.

In still another embodiment of the invention, a method of preventing or treating a mammal for a neurodegenerative disease caused by glutamate neurotoxicity, in particular preventing or treating a neurodegenerative disease such as Huntington's disease, Alzheimer's disease and Parkinson's disease in a human patient, is provided, which method comprises administering a therapeutically effective amount of an NOS inhibitor.

It has been discovered that NO mediates glutamate neurotoxicity and that inhibitors of NOS can be used to prevent neuronal cell death by preventing neurotoxicity mediated through glutamate receptors. Since glutamate neurotoxicity is implicated in vascular stroke and neurodegenerative disorders, such as Alzheimer's disease and Huntington's disease, NOS inhibitors can be used therapeutically in such conditions.

BRIEF DESCRIPTION OF THE DRAWINGS

FIGS. 4A-4P are photomicrographs of cortical cell cultures 24 hours after treatment for NMDA toxicity with various agents.

DETAILED DESCRIPTION OF THE INVENTION

It has been discovered that NOS inhibitors may be used to prevent neuronal cell death. It has now been found that NO mediates glutamate neurotoxicity and that NOS inhibitors may be used therapeutically to prevent neurotoxicity.

NOS inhibitors may be used to prevent, treat, arrest, or ameliorate the progression of any disease condition caused by glutamate neurotoxicity. Such conditions include vascular strokes and neurodegenerative diseases, such as Alzheimer's, Huntington's and Parkinson's diseases, as well as other disease states. For example, following the symptoms of a stroke, a patient is administered an NOS inhibitor to block damage to the brain. Patients with symptoms of Alzheimer's or Huntington's disease are treated with NOS inhibitors to halt the progression of the disease. The symptoms of these disease states are known by one skilled in this art.

Inhibitors of NOS are compounds which compete for the substrate binding site of NOS or other sites on the enzyme, and include both reversible and irreversible inhibitors. The present invention contemplates the use of any physiologically acceptable inhibitor which inhibits NOS activity. The effectiveness of a compound, and its relative potency as an NOS inhibitor, can be tested and routinely determined by measuring inhibition of NOS activity by monitoring the conversion of arginine to citrulline by NOS in, for example, cerebellar homogenates. A reduction in citrulline formation indicates inhibitory activity of the compound. The percent reduction in citrulline formation, compared to the amount of citrulline formed in the absence of the compound being tested, indicates the potency of the compound as an NOS inhibitor.

Both L-$N^\omega$-nitroarginine ($NO_2Arg$) and L-$N^\omega$-monomethylarginine (MeArg), two NOS inhibitors, have been found to prevent neurotoxicity in proportion to their relative potencies as NOS inhibitors. In addition to $NO_2Arg$ and MeArg, other inhibitors of NOS have been developed. Inhibitors have been prepared from arginine, nitroarginine and guanidinoalkanoic acids, wherein the guanidino group, the amino group, the carboxyl group and the backbone have been systematically altered. Various types of structural alterations affect the selectivity of inhibitors toward brain or macrophage enzyme.

Among the nitroarginine analogs tested, nitroarginine was the most potent inhibitor. In general, the introduction of the nitro group on the guanidine moiety appears to result in selective inhibition of the brain enzyme. Moreover, it was found that the nature of substituents on the $\alpha$-amino group seemed to dictate the inhibition potency of the compounds. Whereas a free $\alpha$-amino group offers good inhibitors with 5 to 200 fold selectivity toward brain, the substitution of the amino group with a bulky protective group, such as benzyloxy, results in total loss of activity. A small substituent, such as a formyl group, appears to be favorable.

In the guanidinoalkanoic acid series, it has been found that 6-guanidinohexanoic acid (6-GHA) and 5-guanidinopentanoic acid (5-GPA) are potent inhibitors and show good selectivity toward the macrophage enzyme but were inactive against the brain NOS. The nitro analogs of 6-GHA and 5-GPA were found to be generally inactive, as were guanidinoalkanoic acid analogs made rigid by the cyclization of the guanidino group.

The dosage and length of treatment depends on the disease state being treated. The duration of treatment may be a day, a week or longer and may, as in the case of a chronic progressive illness, such as Alzheimer's, last over the entire lifetime of the patient. The inhibitors are administered in a therapeutically effective amount, a typical human dosage of $NO_2Arg$ ranging from about 0.01 mg/kg of body weight of $NO_2Arg$ to about 10 mg/kg of $NO_2Arg$, in single or divided doses. The dosage will vary depending on the NOS inhibitor to be used and its relative potency. Dosage and length of treatment are readily determinable by the skilled practitioner based on the condition and stage of disease.

In therapeutic use, NOS inhibitors may be administered by any route whereby drugs are conventionally administered. Such routes of administration include intraperitoneally, intravenously, intramuscularly, subcutaneously, intrathecally and intraventricularly, as well as orally.

Typical preparations for administration include sterile aqueous or nonaqueous solutions, suspensions and emulsions. Examples of nonaqueous solvents are propylene glycol, polyethylene glycol, vegetable oils such as olive oil and injectable organic esters such as ethyl oleate. Aqueous carriers include water alcoholic/aqueous and buffered media. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Oral preparations, such as in capsules, tablets, and other forms, include additives such as cellulose, silica gel and stearic acid.

To be effective therapeutically, an NOS inhibitor desirably should be able to penetrate the blood brain barrier when peripherally administrated. However, because of the charged guanidino group, most arginine derivatives would not be expected to penetrate into the brain. Arginine itself has only poor access to the brain following peripheral administration. It is an unexpected discovery that arginine derivatives exist which are able to penetrate into the brain and inhibit enzyme activity in the brain. The finding that the peripheral administration of as little as 5 mg/kg of $NO_2Arg$ markedly inhibits enzyme activity in the brain is unexpected. It may be that the nitro group facilitates penetration of the blood brain barrier and access to the brain following peripheral administration. NOS inhibitors which are unable to penetrate the blood brain barrier can be effectively administered by, for example, an intraventicular route of delivery.

The following examples are provided to exemplify various aspects of the invention and are not intended to limit the scope of the invention.

EXAMPLE 1

This example demonstrates the inhibition of brain NOS by arginine and its analogs.

Rat cerebella were homogenized in 10 vols. (w/v) 20 ml Tris (pH 7.4), 2 mM EDTA. Homogenates were centrifuged at $10,000 \times g$ for 15 minutes at 4° C. Supernatant preparations were used in the enzyme assays. Cerebellar tissue was dialyzed (Spectra/Por, 10,000 MWCO, EDTA-treated cellulose dialysis tubing) against 20 mM Tris (pH 7.4), 2 mM EDTA (300 ml.×2) for 24 hours at 4° C.

Cerebellar homogenates were incubated with arginine derivatives for one hour at 4° C., and dialyzed overnight. Aliquots (25 μg protein) were assayed for NOS activity before and after dialysis.

NOS activity was measured by monitoring the conversion of [$^3$H]arginine to [$^3$H]citrulline as described by Bredt and Snyder (Proc. Natl. Acad. Sci USA (1990) 87682-685). Briefly, enzyme assays contained 25 μl of soluble tissue, 50 μl of 100 mM [$^3$H]arginine and 1 mM NADPH, and 25 μl of 3 mM $CaCl_2$. After a 15 minute incubation at room temperature, the assays were terminated with 3 ml of 20 mM Hepes (pH 5.5) with 2 mM EDTA, and were applied to 0.5 ml columns of Dowex AG50WX8 ($Na^+$ form). [$^3$H]citrulline was quantified by liquid scintillation spectroscopy of the 3 ml flow-through.

Figure 1:
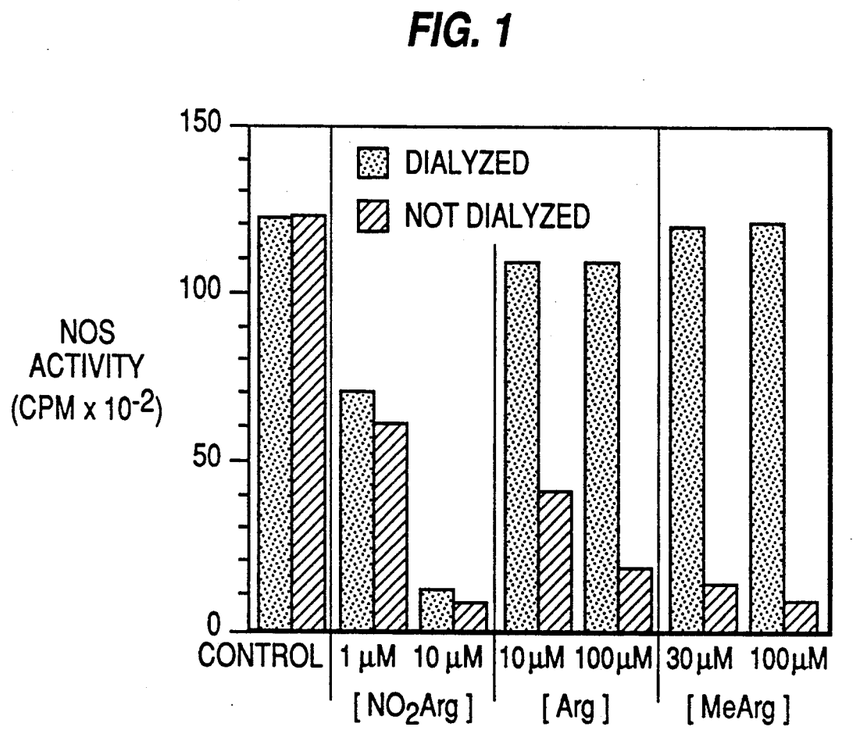
FIG. 1 shows the irreversible inhibition of cerebellar NOS by $NO_2Arg$ in vitro.

As shown in FIG. 1, in cerebellar supernatant preparations, $NO_2Arg$ is a more potent inhibitor of NOS activity than MeArg, while arginine is yet less potent in reducing the conversion of [$^3$H]arginine to [$^3$H]citrulline.

EXAMPLE 2

This example demonstrates an irreversible and selective inhibition of NOS by nitroarginine in vitro.

If $NO_2Arg$ irreversibly inhibits NOS by forming a covalent link, greater inhibition with a more prolonged exposure of the enzyme to the inhibitor would be expected. Accordingly, the effects of 2, 4 and 24 hours of preincubations of cerebellar supernatants (FIG. 2A) and activated macrophage homogenates (FIG. 2B) with $NO_2Arg$ were examined. The preincubation was conducted at 4° C. since NOS is unstable at higher temperature for long periods of time. Enzymatic incubation was conducted for only 5 minutes to minimize any reaction of the inhibitor with the enzyme in the course of the incubation procedure.

Cerebellar supernatants were made as described in Example 1.

Macrophages were activated as described by Tayeh and Marletta (J. Biol. Chem. (1989) 264:19654-19658) with 3.5 ng/ml LPS from $E.$ $coli$ and 5 units/ml recombinant murine γ-interferon for 24 hours at 37° C. Cells were homogenized in 20 mM Hepes (pH 7.4).

Figure 2A:
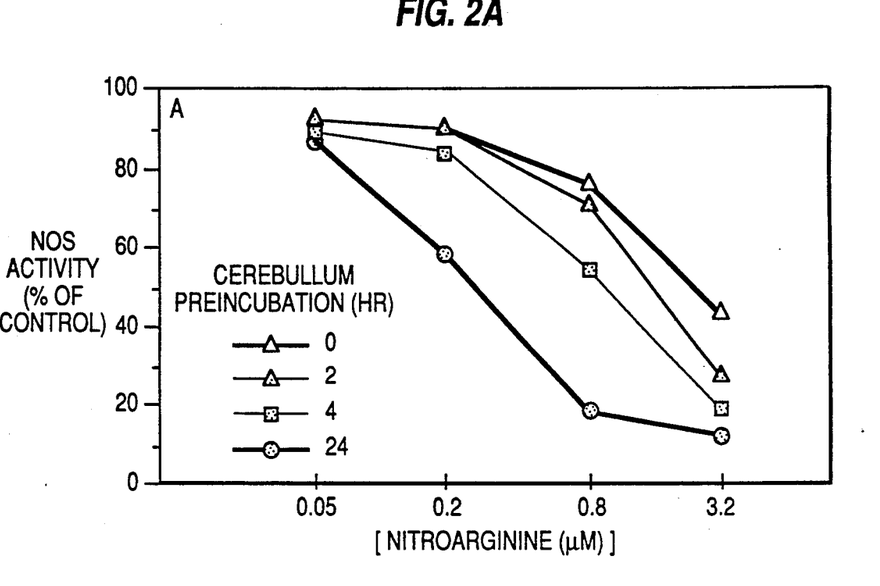
FIGS. 2A and 2B show the time dependent inhibition of cerebellar NOS by $NO_2Arg$ in cerebellar and activated macrophage homogenates, respectively.

As shown in FIG. 2A, preincubation of enzyme with $NO_2Arg$ increases the potency of inhibition with as little as 2 hour preincubation. Preincubation for 24 hours augments the potency of $NO_2Arg$ about 15 times.

Figure 2B:
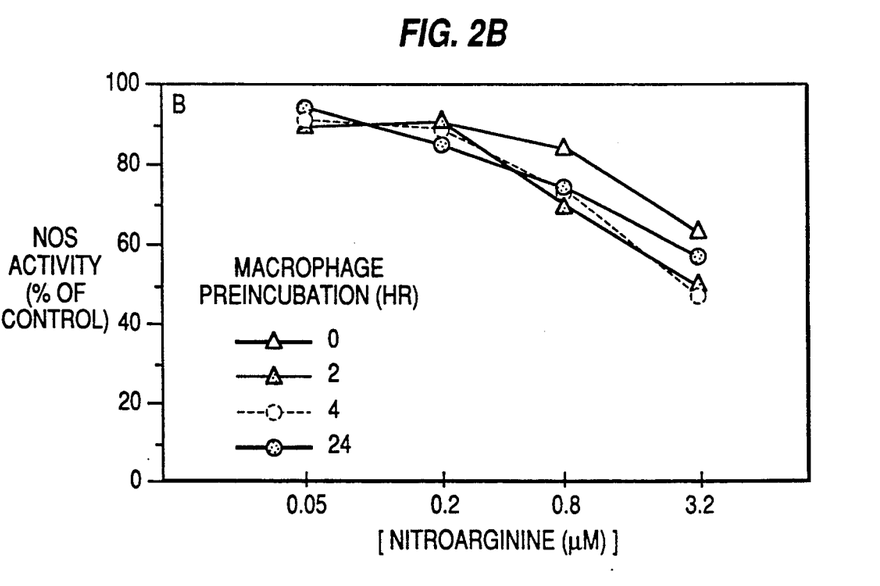

$NO_2Arg$ is a weaker inhibitor of the macrophage enzyme then of the brain-endothelial enzyme (Gross et al. (1990) Biochem. Biophys. Res. Comm. 170:96-103). FIG. 2B shows that in supernatant preparations of activated macrophage cultures, $NO_2Arg$ is a less potent inhibitor of NOS than in cerebellar preparations and that only a minimal enhancement of potency is apparent after preincubation of $NO_2Arg$ with the enzyme at 24 hours. With 24 hours of incubation, $NO_2Arg$ is only about 7% as potent in inhibiting the macrophage enzyme compared to the cerebellar enzyme.

In most studies showing a 10-300 fold greater potency of $NO_2Arg$ in inhibiting brain-endothelial than macrophage NOS (Gross (1990) Biochem. Biophys. Res. Comm. 170:96-103), incubations are conducted at 37° C. for about ½ hour. A 30 minute incubation at 37° C. should therefore be sufficient for $NO_2Arg$ to maximally inhibit the brain-endothelial enzyme.

EXAMPLE 3

This example demonstrates the ability of nitroarginine to penetrate the blood-brain barrier.

Adult male rats (Sprague-Dawley, 3 per group) were injected intraperitoneally (i.p.) twice daily with 5 mg/kg or 50 mg/kg of $NO_2Arg$, MeArg, arginine or vehicle twice a day for four consecutive days. The animals were sacrificed by decapitation 14 hours following the last injection.

Figure 3:
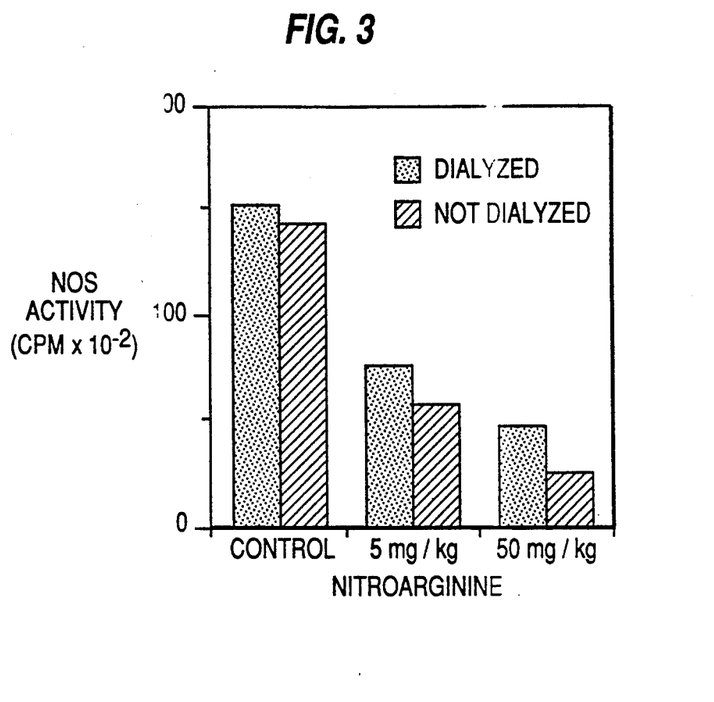
FIG. 3 shows the irreversible inhibition of NOS by $NO_2Arg$ in vivo.

FIG. 3 shows the irreversible inhibition of NOS by $NO_2Arg$ in vivo. Cerebellar homogenates were used to determine NOS activity. Samples (25 μg protein) were assayed for NOS activity before and after dialysis.

At 5 mg/kg $NO_2Arg$ inhibits brain NOS by about 50%. At 50 mg/kg enzyme activity is inhibited 95%. Dialyzing crude supernatant preparations for 24 hours only slightly increases enzyme activity in animals treated with $NO_2Arg$.

It was found that repeated drug administration for 7 days produces no greater inhibition of NOS activity than 4 days of treatment. A single injection of 50 mg/kg was found to reduce enzyme activity by 50%.

EXAMPLE 4

This example demonstrates that nitroarginine does not affect expression of NOS.

To determine whether $NO_2Arg$ administration alters levels of NOS protein, Western blot analysis of brain extracts were performed following the i.p. administration of both 5 and 50 mg/kg of $NO_2Arg$. Soluble cerebellar homogenates (100 μg) were separated on a 7.5% SDS-polyacrylamide gel and transferred to nitrocellulose. Lanes were incubated overnight with affinity purified NOS antibody (1:2500) at room temperature, and bands were visualized with an alkaline phosphatase linked secondary antibody. No alterations in NOS protein were observed. Therefore, the loss of NOS activity following peripheral administration of $NO_2Arg$ is not attributed to inhibition of the synthesis of enzyme protein.

Inhibition of NOS in vivo with $NO_2Arg$ provides a means to evaluate the turnover rate of the enzyme. It has been shown that following 90% inhibition of enzyme activity with 50 mg/kg $NO_2Arg$, brain NOS activity does not return to normal levels for at least 5 days.

The irreversible inhibition of NOS by $NO_2Arg$ both in vivo and in vitro, as shown in Examples 1-4, suggest that $NO_2Arg$ forms a covalent linkage with the enzyme. Example 3 demonstrates the unexpected finding that arginine derivatives are able to penetrate into the brain and inhibit enzyme activity in the brain.

In Examples 5-10, rat primary cortical cultures were employed in order to ascertain the relationship of NO to glutamate neurotoxicity and to demonstrate that glutamate neurotoxicity is prevented selectively by inhibitors of NOS. Primary dissociated cell cultures were prepared from fetal rats (13-to 14-day gestation for cortex and caudate-putamen cultures and 19- to 20-day gestation for hippocampal cultures). The tissue of interest was dissected, incubated for 15 minutes in 0.027% trypsin in Brooks-Logan solution (5% phosphate-buffered saline/0.04M sucrose/10 mM Hepes/0.03M glucose, pH 7.4), and then transferred to modified Eagle's medium (MEM) 10% horse serum/10% fetal bovine serum/2 mM glutamine for trituration. Dissociated cells were plated at a density of $3-4 \times 10^5$ cells per well in polyornithine-coated 15-mm multiwell plates. After 4 days the cells were treated with 10 μg of 5-fluoro-2'-deoxyuridine to prevent proliferations of nonneuronal cells. Cells were maintained in MEM/5% horse serum/2 mM glutamine in 8% $CO_2$/humidified atmosphere at 37° C. The medium was changed twice weekly. Mature neurons (3-4 weeks) were used.

These examples show that NOS inhibitors $NO_2Arg$ ($EC_{50}=20$ μM) and MeArg ($EC_{50}=170$ μM) prevent neurotoxicity elicited by N-methyl-D-aspartate and related excitatory amino acids.

EXAMPLE 5

Cells were exposed to excitatory amino acids according to the method of Koh and Choi (J. Neurosci. (1988) 8:2153-2163). Before exposure, the cells were washed three times with Tris-buffered control salt solution (CSS), containing 120 mM NaCl/5.4 mM KCl/1.8 mM $CaCl_2$/25 mM Tris hydrochloride, pH 7.4 at room temperature/15 mM glucose. Brief exposures to glutamate, NMDA (plus 10 μM glycine), quisqualate, and sodium nitroprusside (SNP) were performed for 5 minutes in CSS. The exposure solution was then washed away and replaced by MEM with 21 mM glucose; then the cells were placed in an incubator for 20-24 hour. Long exposures to kainate were performed in MEM/21 mM glucose for 20-24 hour in the incubator. After exposure to the excitatory amino acids, the medium was replaced by CSS/0.4% trypan blue, which stains nonviable cells. Two to four photographs (10-20×) were made of each well, and viable versus nonviable cells were counted.

The cytotoxicity data represent 6-24 separate wells assayed per data point, with ≈500-1500 cells counted per well. Neuronal cell injury was also assessed by measuring the release of lactate dehydrogenase by damaged or destroyed cells into the extracellular fluid following drug exposure.

For determination of cGMP the cells were washed three times with CSS. After a 1-minute exposure to drug solutions the cells were inactivated with 15% trichloroacetic acid. After ether extraction, cGMP levels were determined by RIA. [$^3H$]MK-801 binding to the NMDA receptor/channel complex was assayed, as described by Javitt and Zukin (Proc. Natl. Acad. Sci. USA (1989) 86:740-744). NO synthase activity was assayed by the conversion of [$^3H$]arginine to [$^3H$]citrulline (Bredt and Snyder (1989) Proc. Natl. Acad. Sci. USA 86:9030-9033 and Bredt and Snyder (1990) Proc. Natl. Acad. Sci USA 87:682-685). For immunoblots, 200-400 μg of crude tissue protein was separated on a 7.5% SDS/polyacrylamide gel and transferred to nitrocellulose. Lanes were incubated with affinity-purified antibody (1:1000) (Bredt et al. (1990) Nature 347:768-770).

Before initiating cytotoxicity experiments with NOS inhibitors, the potency of NMDA applied for 5 minutes in inducing cell death was evaluated by examining exclusion of 0.4% trypan blue by viable cells or measuring lactate dehydrogenase released by damaged or destroyed cells into the extracellular fluid. As previously reported by Koh and Choi (J. Neurosci. (1988) 8:2153-2163), NMDA displays a toxic $LD_{50}$ of 280 μM, and 300 μM NMDA consistently yields 60% cell death.

Simultaneous application of 100 μM $NO_2Arg$, a potent NOS inhibitor (Heckler et al. (1990) Biochem. Biophys. Res. Commun. 167:1037-1043 and Dwyer et al. (1991) Biochem. Biophys. Res. Commun. 176:1136-1141), with NMDA reduces cell death by 70%. Addition of 1 mM L-arginine (L-Arg) to the exposure solution completely reverses the effect of $NO_2Arg$.

To further ascertain whether NO is involved in NMDA neurotoxicity 500 μM of reduced hemoglobin (Hb), which binds NO, was added simultaneously with 300 μM NMDA. Hb completely prevents NMDA-induced cell death at 500 μM, similar to the concentration required for reduced myoglobin to prevent macrophage-mediated cell death (Stuehr and Nathan (1989) J. Exp. Med. 169:1543-1555).

FIGS. 4A-4F shows bright-field photomicrographs of cortical cell cultures 24 hour after treatment and after 0.4% trypan blue dye exclusion to stain nonviable cells. Dead cells appear as black dots, and live cells appear as raised cells against the gray background.

Figure 4:
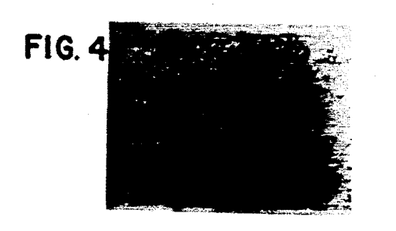

(A) Control.

(B) NMDA (300 μM plus 10 μM glycine).

(C) NMDA (300 μM plus 10 μM glycine) plus 100 $NO_2Arg$ demonstrates inhibition of NMDA cytotoxicity.

(D) L-Arg (1 mM) reverses the inhibition by 100 μM $NO_2Arg$ of 300 μM NMDA (plus 10 μM glycine) cytotoxicity.

(E) Treatment of cell cultures for 24 hour in L-Arg-free medium abolishes NMDA toxicity.

(F) Reduced Hb plus 300 μM NMDA (with 10 μM glycine) reverses cell death.

EXAMPLE 6

This example shows that in cortical cell cultures, NMDA stimulation of cGMP formation involves NO.

The cortical cultures possess substantial NOS catalytic activity and protein, ≈10% of cerebellar levels. Furthermore, NMDA can stimulate the formation of NO in cortical cultures. Formation of cGMP can be used as an indirect measure of NO formation (Bredt and Snyder (1989) Proc. Natl. Acad. Sci. USA 86:9030-9033 and Garthwaite et al. (1989) Eur. J. Pharmacol. 172:413-416), as NO binds to the heme moiety of guanylate cyclase and subsequently activates the enzyme. As has been shown in cerebellar slices, NMDA stimulation of cGMP levels in cultures is antagonized by inhibiting NOS with $NO_2Arg$ or complexing NO with Hb. $NO_2Arg$ inhibition of cGMP formation by NMDA is competitively reversible by L-Arg. Superoxide dismutase (SOD), which removes superoxide that would degrade NO, potentiates the formation of cGMP by NMDA. Thus, as in cerebellar slices in cortical cell cultures NMDA stimulation of cGMP formation involves NO.

Figure 5:
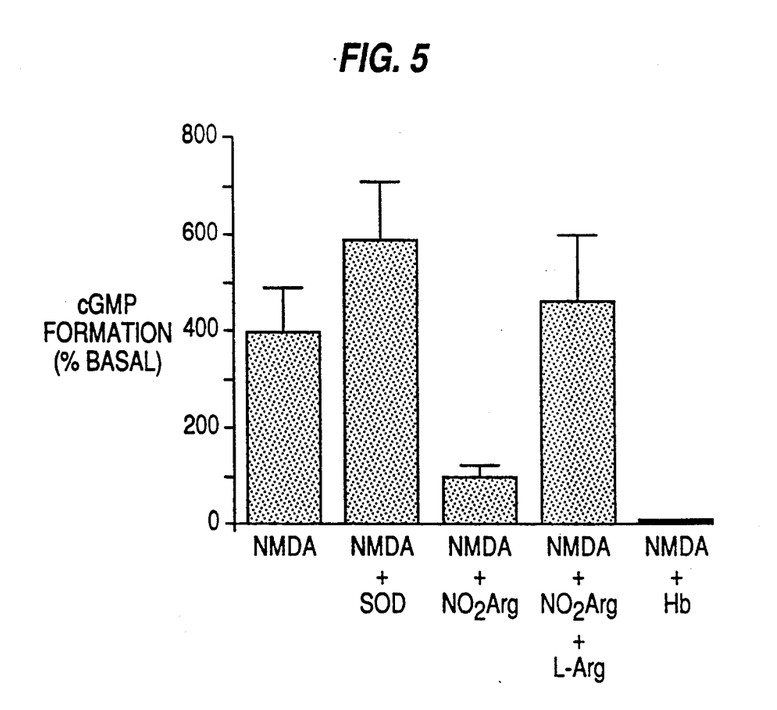
FIG. 5 shows cGMP formation in cortical cell cultures.

FIG. 5 shows cGMP formation after 1-minute application of 300 μM NMDA (plus 10 μM glycine) to cortical cultures with or without 100 μM $NO_2Arg$, 100 μM $NO_2Arg$ plus 1 mM L-Arg, 100 units of SOD, or 500 μM reduced Hb. Basal level of cGMP is 1.5 pmol/mg of protein. Data are means ±SEM (n=6-8).

EXAMPLE 7

To ascertain the potency of $NO_2Arg$ in preventing cell death, the concentration of $NO_2Arg$ was varied. Approximately 50% prevention of NMDA-induced cell death is evident at 20 μM $NO_2Arg$. The potency of $NO_2Arg$ is similar whether applied simultaneously with NMDA or 5 minutes earlier. Me-Arg, another NOS inhibitor less potent than $NO_2Arg$ (Heckler et al. (1990) Biochem. Biophys. Res. Commun. 167:1037-1043 and Dwyer et al. 91991) Biochem. Biophys. Res. Commun. 176:1136-1141), also prevents NMDA-induced cell death with 50% prevention of death at a concentration of 170 μM.

Figure 6:
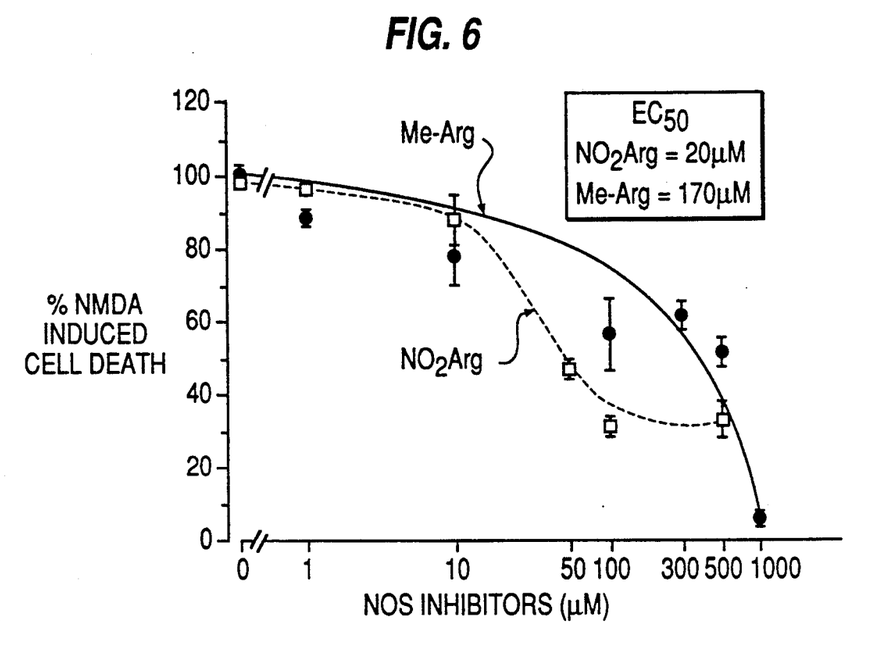
FIG. 6 shows the concentration-response relationship of NOS inhibitors in inhibiting NMDA neurotoxicity.

FIG. 6 shows the concentration-response relationship of NOS inhibitors in inhibiting NMDA neurotoxicity. Data are means ±SEM (n=6).

In inhibiting NOS activity of purified enzyme preparations, $NO_2Arg$ and MeArg have $K_i$ values of 200 nM and 2 μM, respectively (Dwyer et al. (1991) Biochem. Biophys. Res. Commun. 176:1136-1141). The higher concentrations of these inhibitors required to prevent NMDA neurotoxicity probably reflects competition by the high 1 mM L-Arg concentration in the culture medium. Therefore, arginase was added in amounts that should completely degrade L-Arg. Additionally, sister cultures were grown for 24 hour in medium without L-Arg, but containing glutamine, a procedure that fully depletes cells of L-Arg (Sessa et al. (1990) Proc. Natl. Acad. Sci. USA 87:8607-8611). In both arginase-treated preparations and in experiments with L-Arg-free medium, 300 μM NMDA no longer causes cell death (see FIG. 1), and the 50% lethal concentration of NMDA is increased >20-fold to 7.5 mM. Adding graded concentrations of L-Arg to L-Arg-free medium reveals a requirement for 100 μM L-Arg to obtain maximal NMDA effects.

EXAMPLE 8

Glutamate neurotoxicity in primary cortical cultures can be elicited by NMDA, quisqualate, and kainate, although the NMDA receptor presumably accounts for most neurotoxicity associated with synaptically released glutamate in various pathologic conditions (Choi, 91990) J. Neurosci. 10:2493-2501 and Meldrum and Garthwaite (1990) Trends in Pharmacol. Sci. 11:379-387). Quisqualate and kainate act more slowly and less potently than NMDA and via somewhat different mechanisms (Koh et al. (1990) J. Neurosci. 10:693-705).

To examine the role of NO in other forms of glutamate neurotoxicity, the effects of $NO_2Arg$ cytotoxicity induced by quisqualate, kainate, and NMDA were compared. Table 1 shows the inhibition of glutamate neurotoxicity by $NO_2Arg$ and reversal by L-Arg in cortical culture. Data are means ±SEM (n=6-24). Cell death was determined by 0.4% trypan blue exclusion by viable cells.

TABLE 1

|  | Cell death, % ± SEM |
| --- | --- |
| 500 μM glutamate | 48.4 ± 4.4 |
| +100 μN $NO_2Arg$ | 28.9 ± 6.0* |
| +100 μM $NO_2Arg$ + 1 Mm L-Arg | 48.2 ± 3.2 |
| 300 μM NMDA + 10 μM glycine | 57.8 ± 2.6 |
| +100 μM $NO_2Arg$ | 17.7 ± 3.0** |
| +100 μM $NO_2Arg$ + 1mM L-Arg | 63.4 ± 5.5 |
| 500 μM quisqualate | 64.2 ± 3.7 |
| +500 μM $NO_2Arg$ | 51.1 ± 2.4*** |
| +500 μM $NO_2Arg$ + mM L-Arg | 66.6 ± 5.3 |
| 100 μM kainate | 81.4 ± 7.1 |
| +500 μM $NO_2Arg$ | 87.0 ± 3.2 |

Significant overall $F$ values were obtained by using a one-way, between-groups analysis of variance. Specific comparisons on all possible pairwise combinations were made with the Student's $t$ test for independent means, $P < 0.05$, *$F,2,16,29.3,P < 0.001$; $F,2,33,59.7,P < 0.001$; *$F,2,46,6.1,P < 0.005$.

A portion of cell death elicited by quisqualate is prevented by $NO_2Arg$ with reversal by L-Arg, but higher concentrations of $NO_2Arg$ are required than with NMDA toxicity. $NO_2Arg$ provides no protection against kainate-induced cell death. The slight protection afforded by $NO_2Arg$ with quisqualate neurotoxicity may relate to the portion of quisqualate cell death occurring via NMDA receptor activation (Koh et al. (1990) J. Neurosci. 10:693-705). The relative effects of the glutamate analogs and $NO_2Arg$ have been found to be similar in cultures from caudate-putamen, hippocampus, and cerebral cortex.

EXAMPLE 9

To ascertain the specificity of L-Arg in reversing $NO_2Arg$ effects by arginine, L-Arg was compared to homoarginine and D-arginine (D-Arg). Homoarginine can serve as a precursor of NO but has less affinity for NOS than L-Arg (Knowles et al. (1989) Proc. Natl. Acad. Sci. USA 86:5159-5162). Homoarginine reverses effects of $NO_2Arg$ but is less potent than L-Arg. The stereoisomer D-Arg is much weaker than L-Arg, possibly reflecting a 1-2% contamination with L-Arg, as the extent of $NO_2Arg$ reversal by 1 mM D-Arg is comparable to that obtained with 10 μM L-Arg.

Figure 7:
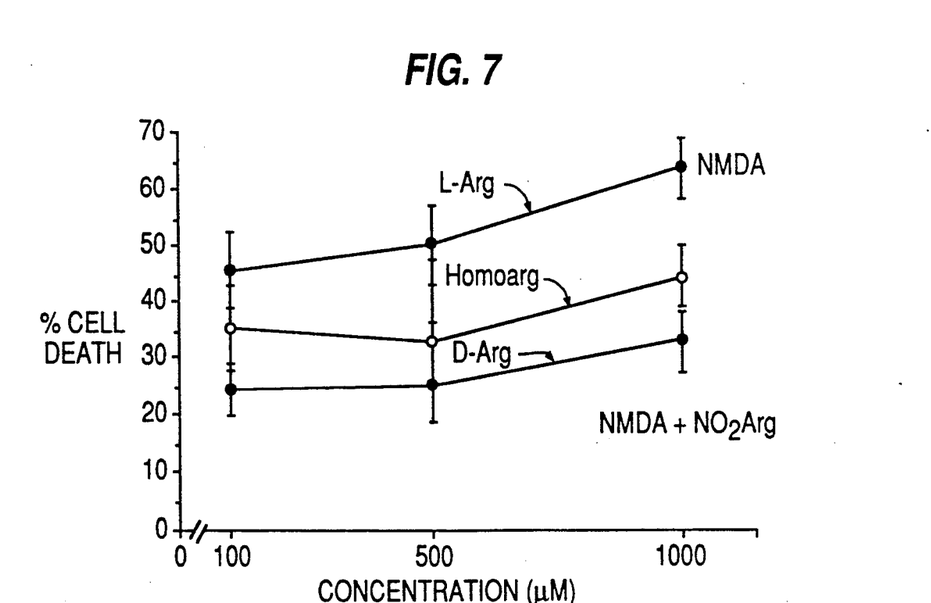
FIG. 7 shows the reversal of $NO_2Arg$ protection from NMDA cytotoxicity by L-arginine, homoarginine and D-arginine.

FIG. 7 shows the selectivity for reversal of $NO_2Arg$ protection from NMDA cytotoxicity by L-Arg, homoarginine (Homoarg), and D-Arg. Solid horizontal lines represent the percent of cell death after exposure to 300 μM NMDA (plus 10 μM glycine) or 300 μM NMDA (with 10 μM glycine) plus 100 μM $NO_2Arg$. Data are means ±SEM (n=6).

EXAMPLE 10

To determine the direct effect of NO upon the cortical cells, the cells were exposed for 5 minutes to sodium nitroprusside (SNP) which spontaneously releases NO, and cell death assessed 24 hour later. SNP elicits cell death in a concentration-dependent fashion with a 50% maximal response at 50 μM. SNP enhances cGMP levels in the cortical cells with similar potency. The influence of SNP on cGMP levels in these cells appears to involve NO, as it is blocked by Hb, which complexes with NO. Furthermore, reduced Hb (500 μM) completely prevents SNP-induced cell death.

Figure 8:
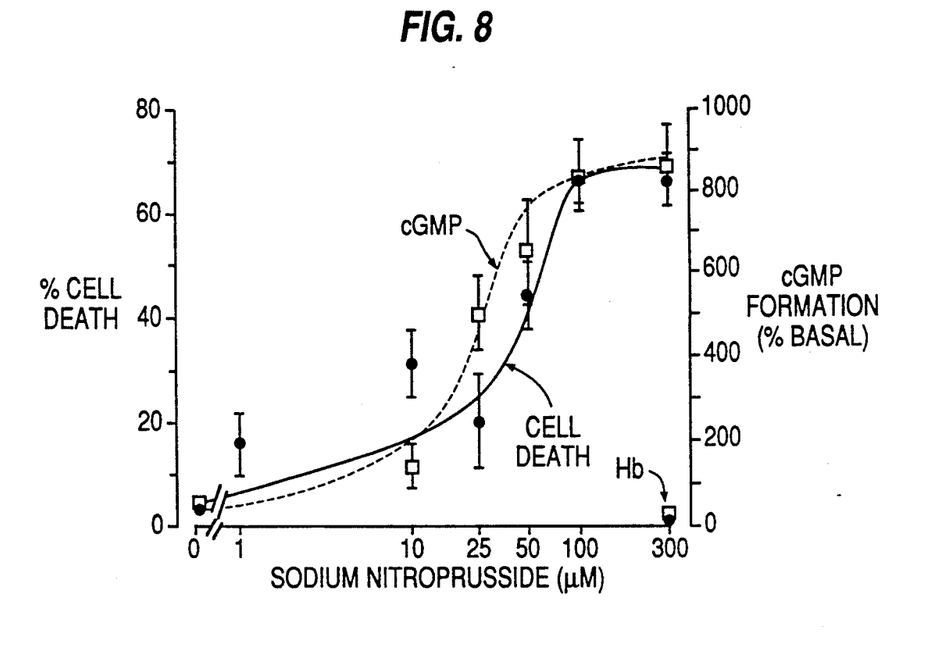
FIG. 8 compares cytotoxicity following exposure to sodium nitroprusside and cGMP formation following exposure to reduced hemoglobin.

FIG. 8 shows comparison of cytotoxicity after 5-minute exposure to SNP and cGMP formation after a 1-minute exposure. Hb (500 μM) completely reverses SNP-mediated cytotoxicity and cGMP formation (arrow). Basal level of cGMP is 1.5 pmol/mg of protein. Data are means ±SEM (n=8–12).

The above examples show that NOS inhibition prevents neurotoxicity elicited by N-methyl-D-aspartate and related excitatory amino acids. This effect is competitively reversed by L-arginine. Depletion of the culture medium of arginine by arginase or arginine-free growth medium completely attenuates N-methyl-D-aspartate toxicity. Sodium nitroprusside, which spontaneously releases NO, produces dose-dependent cell death that parallels cGMP formation. Hemoglobin, which complexes NO, prevents neurotoxic effects of both N-methyl-D-aspartate and sodium nitroprusside. These data establish that NO mediates the neurotoxicity of glutamate and that NOS inhibitors may be used therapeutically to treat neurotoxicity mediated through glutamate receptors.

We claim:

1. A method of preventing or treating a disease condition caused by glutamate neurotoxicity in a mammal comprising:
administering to a mammal in need thereof a therapeutically effective amount of an inhibitor of nitric oxide synthase.

2. The method of claim 1 wherein said inhibitor is administered intravenously, intraperitoneally, intramuscularly or orally.

3. The method of claim 2 wherein said inhibitor is nitroarginine.

4. The method of claim 1 wherein said inhibitor is nitroarginine.

5. The method of claim 1 wherein said inhibitor is a nitroarginine analog.

6. The method of claim 1 wherein said disease is vascular stroke.

7. The method of claim 1 wherein said disease is a neurodegenerative disease.

8. A method of preventing or treating vascular stroke in a human patient comprising:
administering to a human patient a therapeutically effective amount of an inhibitor of nitric oxide synthase.

9. The method of claim 8 wherein said inhibitor is administered intravenously, intraperitoneally, intramuscularly or orally.

10. The method of claim 9 wherein said inhibitor is nitroarginine.

11. The method of claim 8 wherein said inhibitor is nitroarginine.

12. The method of claim 8 wherein said inhibitor is a nitroarginine analog.

13. A method of treating a neurodegenerative disease in a human patient comprising:
administering to a human patient a therapeutically effective amount of an NOS inhibitor.

14. The method of claim 13 wherein said inhibitor is administered intravenously, intraperitoneally, intramuscularly or orally.

15. The method of claim 14 wherein said inhibitor is nitroarginine.

16. The method of claim 13 wherein said inhibitor is nitroarginine.

17. The method of claim 13 wherein said inhibitor is a nitroarginine analog.

18. The method of claim 13 wherein the neurodegenerative disease is Huntington's disease, Alzheimer's disease or Parkinson's disease.

* * * * *